United States Patent
Pajunk et al.

(10) Patent No.: US 8,142,417 B2
(45) Date of Patent: Mar. 27, 2012

(54) CLAMP ADAPTER FOR A CATHETER

(75) Inventors: Horst Pajunk, Geisingen (DE);
Heinrich Pajunk, Geisingen (DE)

(73) Assignee: Pajunk GmbH & Co. KG Besitzverwaltung (DE)

( * ) Notice: Subject to any disclaimer, the term of this patent is extended or adjusted under 35 U.S.C. 154(b) by 0 days.

(21) Appl. No.: 12/602,924

(22) PCT Filed: Jun. 16, 2008

(86) PCT No.: PCT/EP2008/004825
§ 371 (c)(1),
(2), (4) Date: Dec. 3, 2009

(87) PCT Pub. No.: WO2009/000439
PCT Pub. Date: Dec. 31, 2008

(65) Prior Publication Data
US 2010/0191193 A1 Jul. 29, 2010

(30) Foreign Application Priority Data
Jun. 22, 2007 (DE) .......................... 10 2007 029 229

(51) Int. Cl.
*A61M 25/16* (2006.01)
(52) U.S. Cl. ......... 604/533; 604/534; 604/535; 604/536

(58) Field of Classification Search ................... 604/246, 604/250, 533; 606/1, 151, 157, 277, 324; 30/189
See application file for complete search history.

(56) References Cited

U.S. PATENT DOCUMENTS

| 4,187,848 A | 2/1980 | Taylor |
| 5,125,915 A | 6/1992 | Berry et al. |
| 6,350,260 B1 | 2/2002 | Goebel et al. |
| 6,572,590 B1 * | 6/2003 | Stevens et al. ............... 604/246 |
| 2002/0069537 A1 * | 6/2002 | Wenzler .......................... 30/189 |
| 2003/0181892 A1 * | 9/2003 | Pajunk et al. ..................... 606/1 |
| 2004/0039373 A1 * | 2/2004 | Harding et al. ............... 604/533 |

FOREIGN PATENT DOCUMENTS
DE 20305061 8/2004
* cited by examiner

*Primary Examiner* — Kevin C Sirmons
*Assistant Examiner* — Bradley Thomas, Jr.
(74) *Attorney, Agent, or Firm* — Akerman Senterfitt; Peter A. Chiabotti

(57) ABSTRACT

A clamp adapter for a catheter that has a clamp body that receives an elastomeric clamp bushing. In order to fix a catheter inserted into the clamp bushing, the clamp bushing is axially compressed by a clamp lid. For this purpose, the clamp lid is moved axially on the clamp body with a clamp lever by means of a slotted guide.

10 Claims, 6 Drawing Sheets

Figure 1:
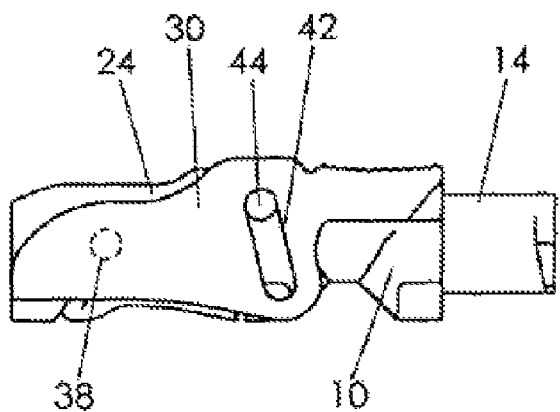

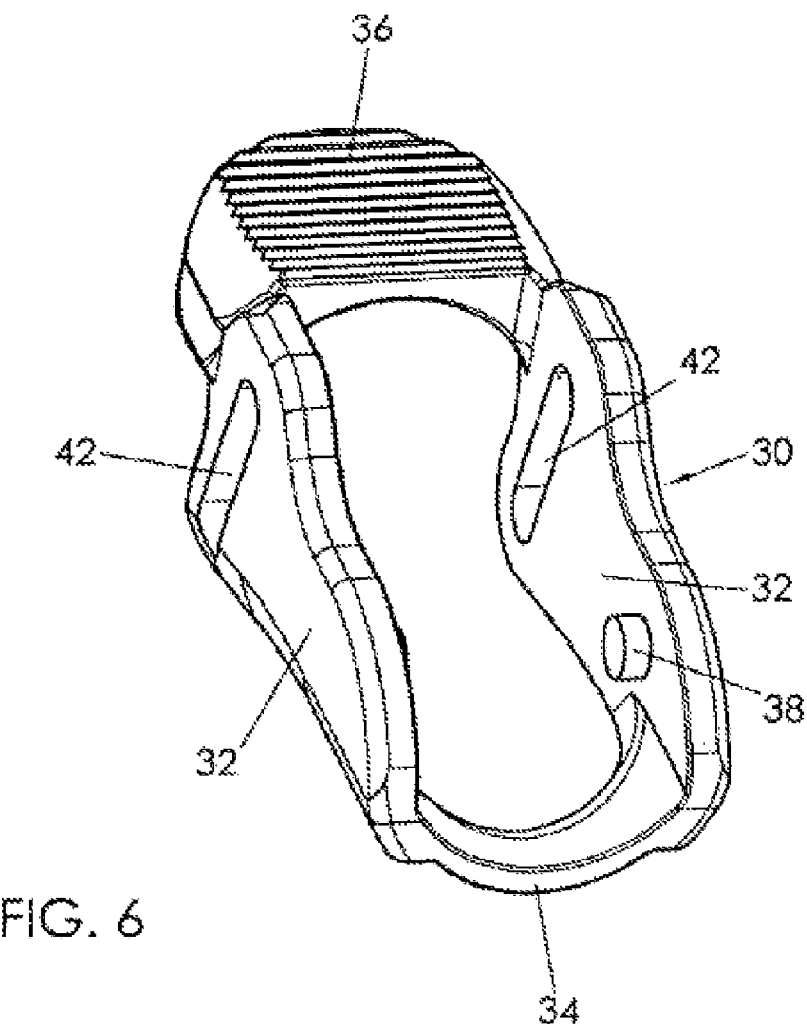
FIG. 6
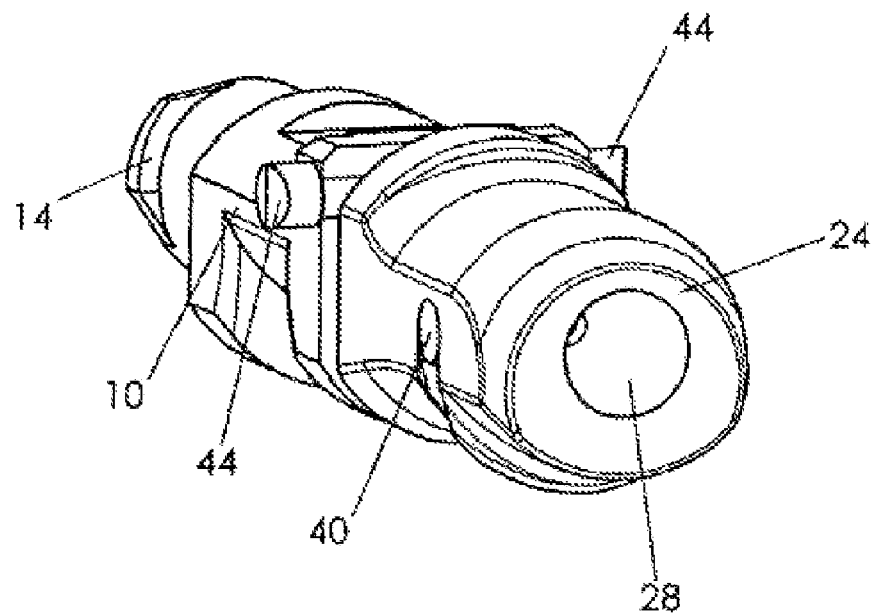

CLAMP ADAPTER FOR A CATHETER

The invention relates to a clamp adapter for a catheter according to the preamble of claim 1.

In anesthesia, for lengthy operations, for postoperative pain therapy, and for the treatment of chronic pain conditions, the nerves supplying a specific region of the body are blocked by the introduction of an anesthetic. A catheter is used to introduce the anesthetic or other liquid, the distal end of which catheter is positioned as closely as possible to the nerve to achieve an optimum effect with the smallest possible quantity of anesthetic. The catheter comprises a long, thin, flexible plastic tube so that it is possible to place the catheter in the desired location and for it to remain in position for a long time, if necessary.

In order to be able to insert the flexible catheter into the perineurium or the neural canal, a cannula is used, which is inserted into the perineurium or the neural canal and through which the catheter is then inserted. In order to apply a liquid, for example, an anesthetic, through the catheter, a syringe is attached to the proximal end of the catheter that remains outside the body. An adapter fitted to the proximal end of the catheter is used for this purpose. If the catheter is to remain in position for a lengthy period of time, the cannula serving to introduce the catheter must be withdrawn. To this end it is necessary to remove the adapter from the catheter so that the cannula can be withdrawn via the proximal end of the catheter. In order to add further anesthetic through the catheter that is in position, after the cannula has been withdrawn the adapter must be re-attached to the end of the catheter.

In order to attach the adapter to the end of the catheter in a simple and detachable manner, the use of a clamp adapter of the type referred to at the outset is known from DE 101 00 975 C1. In the case of this clamp adapter, a hollow cylindrical clamping bush made of a flexibly yielding material is inserted into a clamping body. The proximal end of the catheter is fed coaxially into this clamping bush. Then the clamping bush is axially compressed by a clamping lid placed on the clamping body, whereby the inside diameter of the clamping bush is reduced and the catheter is fixed and sealed on its external circumference. With this known clamp adapter, the clamping lid can be moved axially on the clamping body by means of a screw thread to compress the clamping bush.

A clamp adapter for a catheter is known from EP 1 033 146 B1, which has two jaws that can be pivoted towards one another and engaged with one another, between which a hose piece is arranged, which accommodates the proximal end of the catheter.

The object of the invention is to provide a clamp adapter, which renders possible a simple and reliable fixing of the catheter end in the clamp adapter.

This object is attained according to the invention by a clamp adapter with the features of claim 1.

Advantageous embodiments and further developments of the invention are disclosed in the subordinate claims.

In the case of the clamp adapter according to the invention, the proximal end of the catheter is accommodated in a non-rigid clamping bush and fixed by axial compression of the clamping bush. A clamping lever is used to compress the clamping bush, which clamping lever can be pivoted about a pivot axis running transversely to the longitudinal axis of the clamp adapter. During this swivel motion, the clamping lever causes a mutual axial linear displacement of the clamping lid and the clamping body by means of a sliding block guide. The clamp adapter can thus be brought from an open position into a clamping position and vice versa by means of a simple pivoting of the clamping lever. The clamping bush is axially unloaded in the open position so that the catheter can be inserted or the clamp adapter can be withdrawn from the catheter end. In the clamping position, the clamping bush is axially compressed and clamps the proximal end of the catheter to the outer circumference thereof. The two pivot positions of the clamping lever are clearly mechanically defined, so that in particular the attachment of the clamp adapter to the catheter end is possible in a simple and reliable manner solely by pivoting the clamping lever into its dead-center position in the clamping position.

The clamping lever is preferably swivel-mounted on the clamping lid, wherein the sliding block guide is embodied between the pivoted lever and the clamping body. Of course, a swivel mounting of the clamping lever on the clamping body is also possible, wherein the sliding block guide is then embodied between the clamping lever and the clamping lid.

In an advantageous embodiment, the sliding block guide is formed by a guideway running obliquely to the longitudinal axis and a pilot pin running in this guideway. Preferably the guideway is embodied in the clamping lever, e.g., as a longitudinal slot and the pilot pin is embodied accordingly on the clamping body or the clamping lid. Of course, an inverse embodiment of the guideway on the clamping body or the clamping lid and of the pilot pin on the clamping lever is also possible here.

It is expedient if the clamping lever is embodied with the sliding block guide such that in the open position it is braced by the clamp adapter and in the clamping position it bears against the clamp adapter. This ensures that with the fixed catheter the clamping lever is not in the way and is not accidentally pivoted into the open position.

The clamp adapter can be embodied for a simple catheter and likewise for a stimulation catheter. In the embodiment for a stimulation catheter, the clamping body has a contact bush adjoining the clamping bush proximally, which contact bush, when the catheter is inserted, contacts an electrically conducting stimulation wire of the catheter and can be connected via a plug and socket connector to an electrical stimulation device.

Figure 2:
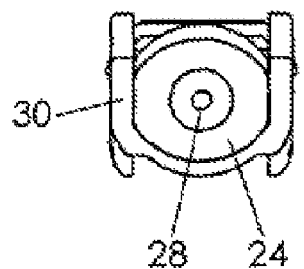
Figure 3:
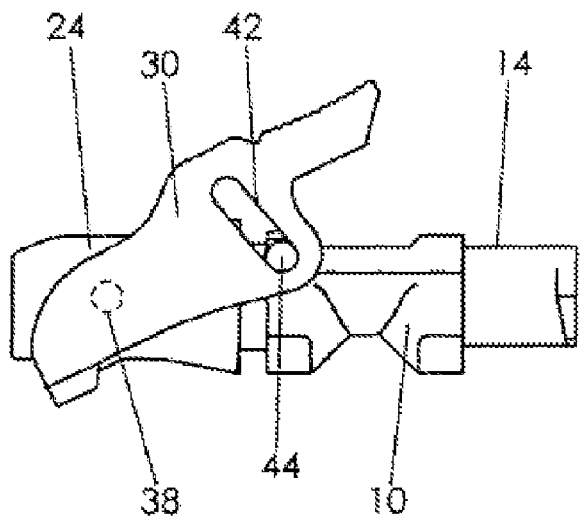
Figure 4:
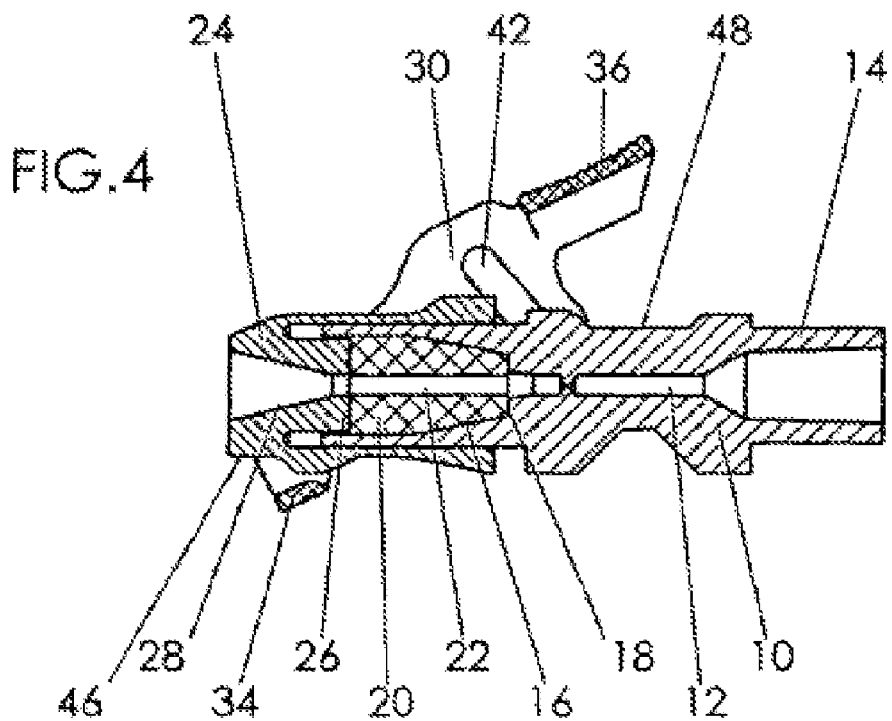
Figure 5:
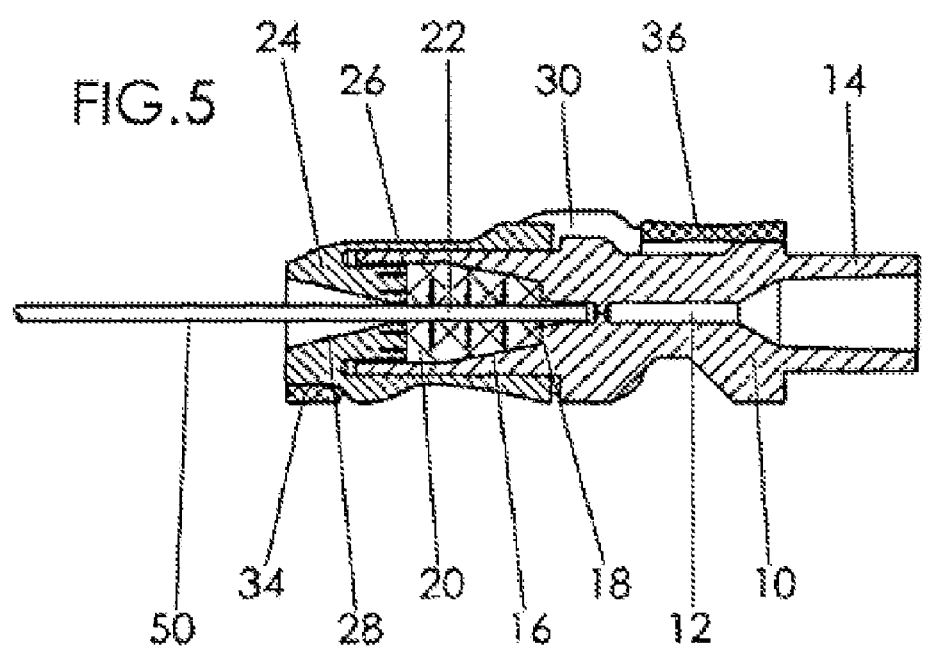

The invention is explained in more detail below based on exemplary embodiments shown in the drawing. They show:

FIG. 1 A side view of the clamp adapter in a first embodiment in the clamping position, FIG. 2 A front view of the distal end of the clamp adapter, FIG. 3 A side view of the clamp adapter in the open position, FIG. 4 An axial section of the clamp adapter in the open position, FIG. 5 An axial section of the clamp adapter in the clamping position.

FIG. 6 A perspective exploded view of the clamp adapter

Figure 7:
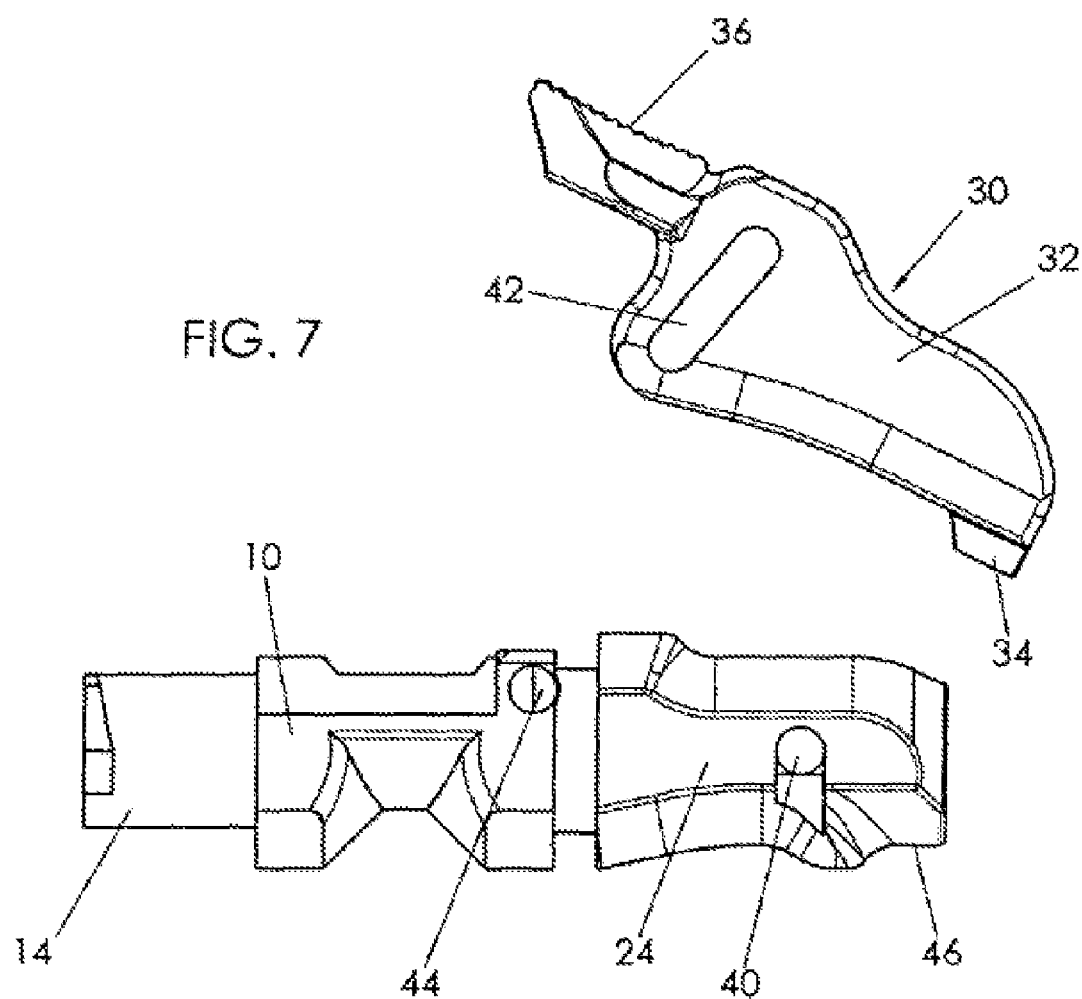
Figure 8:
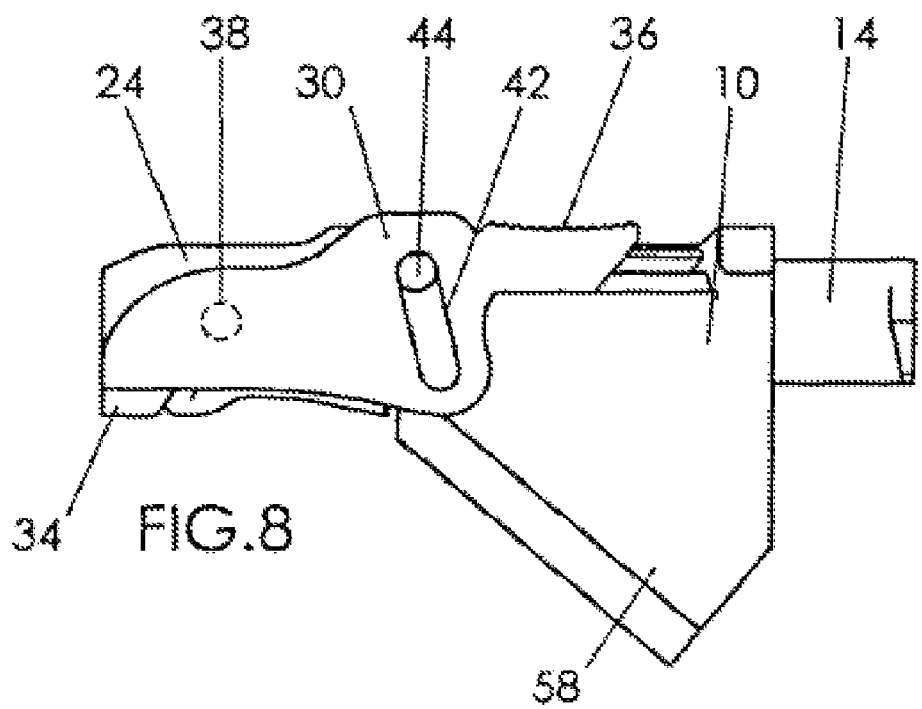
Figure 9:
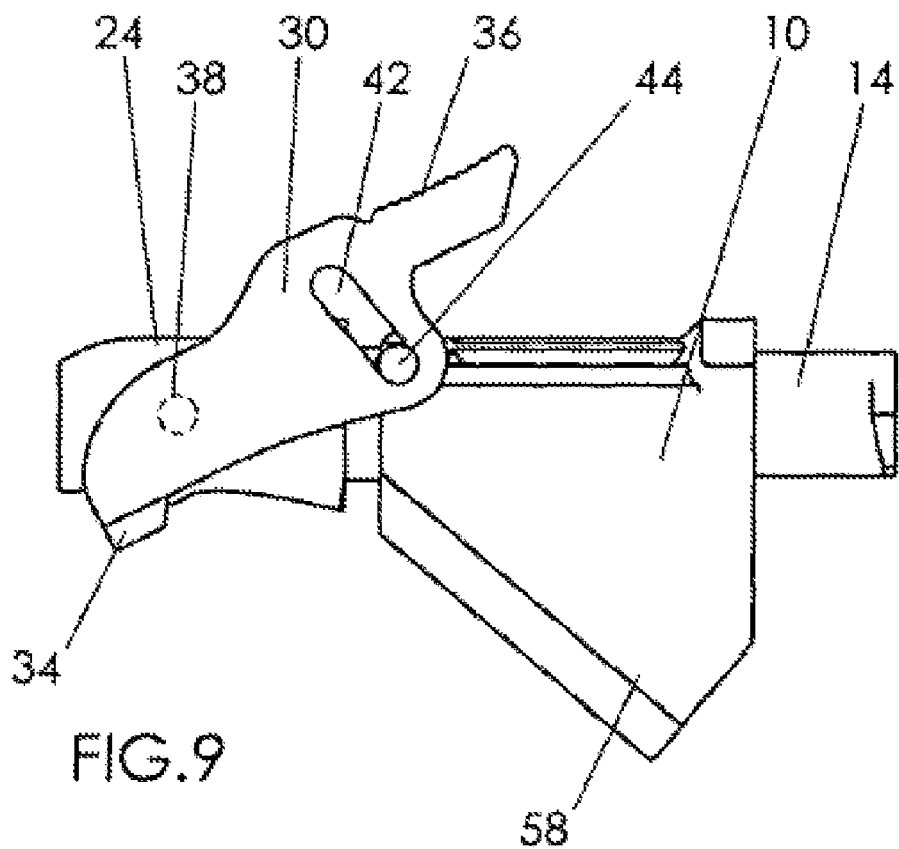
Figure 10:
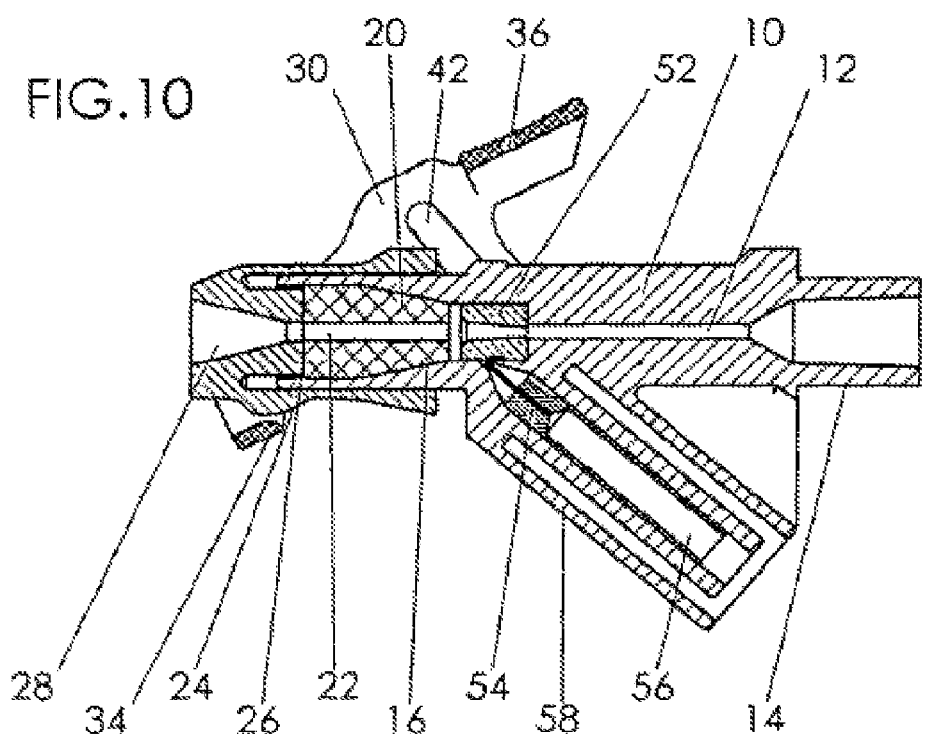
Figure 11:
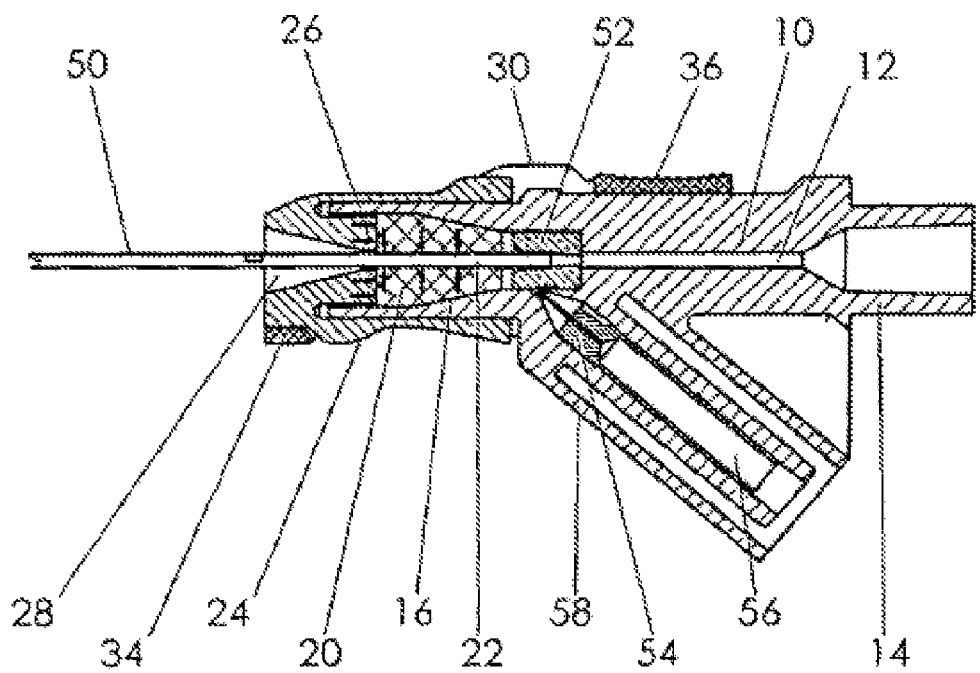

FIG. 7 A side view of the clamp adapter in exploded view,

FIG. 8 A side view of the clamp adapter in a second embodiment in the clamping position, FIG. 9 A side view of the clamp adapter in the second embodiment in the open position, FIG. 10 An axial section of the clamp adapter in the second embodiment in the open position and FIG. 11 An axial section of the clamp adapter in the second embodiment in the clamping position.

In FIGS. 1 through 7, the clamp adapter is shown in a first standard embodiment for a simple catheter.

The clamp adapter has a clamping body 10, which is preferably a plastic molded part. The clamping body 10 has an axially through hole 12. The proximal end of the clamping body 10 is embodied as a syringe fitting 14, e.g., as a Luer Lock fitting. The proximal end of the bore 12 opens coaxially into the syringe fitting 14. The bore 12 expands distally to form a coaxially aligned receptacle space 16. The transition from the diameter of the bore 12 to the larger diameter of the receptacle space 16 forms a radial inner shoulder 18. The receptacle space 16 firstly expands slightly conically in the distal direction from the inner shoulder 18 and then merges into a cylindrical section.

A clamping bush 20 is placed in the receptacle space 16, which clamping bush comprises a yielding elastomeric plastic. The clamping bush 20 corresponds in its outer circumferential shape to the interior circumferential shape of the receptacle space 16 and is penetrated axially in the center by an inner channel 22, which, when the clamping bush 20 is inserted, adjoins the bore 12 of the clamping body 10 in a coaxially aligned manner. The clamping bush 20 placed in the receptacle space 16 bears against the interior shoulder 18 with its proximal front face, while the distal front face of the clamping bush 20 is displaced inwards with respect to the distal end of the receptacle space 16.

A clamping lid 24, which is likewise a plastic molded part, is placed distally on the clamping body 10. The clamping lid 24 overlaps the distal end of the clamping body 10 in a cup-shaped manner and is guided thereon in an axially displaceable manner. A contact surface 26 is embodied on the clamping lid 24, which contact surface engages in the form of a coaxial cylindrical projection in the distal end of the receptacle space 16. The clamping lid 24 bears against the distal front face of the clamping bush 20 with the contact surface 26. The clamping lid 24 is penetrated axially in the center by an insert opening 28, which narrows in a funnel-shaped manner in the proximal direction to the diameter of the inner channel 22 of the clamping bush 20.

On the clamping lid 24 a clamping lever 30 is swivel-mounted about a pivot axis running perpendicular to the center axis of the clamping body 10. The clamping lever 30 is likewise a plastic molded part. The clamping lever 30 has two side walls 32 bearing against the clamping lid 24 on the right and on the left, which are connected to one another distally on the underside by a transverse bracket 34 and proximally on the top by a transverse bracket 36 embodied as a gripping surface. Journal pins 38 are respectively formed on the inner surfaces of the side walls 32, which journal pins engage in bearing bores 40 in the side surfaces of the clamping lid 24. The journal pins 38 and the bearing bores 40 thus form the pivot axis about which the clamping lever 30 can be pivoted with respect to the clamping lid 24. The clamping lever 30 is snapped onto the clamping lid 24, to which end the side walls 32 are spread apart slightly until the journal pins 38 snap into the bearing bores 40, so that the clamping lever 30 is supported on the clamping lid 24 in a pivoted manner and so that it cannot be lost.

In the proximal region of the clamping lever 30 the side walls 32 respectively bear against the clamping body 10 on the outside and are embodied with guideways 42. The guideways 42 are formed by longitudinal slots in the side walls 32, which run obliquely at an acute angle with respect to the center axis of the clamp adapter, as can be best seen from FIGS. 1 and 3. Pilot pins 44 engage respectively in the guideways 42, which pilot pins are formed on the outsides of the clamping body 10. The guideways 42 and the pilot pins 44 interact as a sliding block guide in the following manner The clamping lever 30 can be pivoted about its pivot axis formed by the journal pins 38 and the bearing bores 40 into an open position shown in FIGS. 3 and 4. In this open position, the proximal end of the clamp lever 30 is braced by the clamping body 10. The pilot pins 44 in this open position reach to the lower end of the guideways 42, wherein the stop of the lower end of the guideways 42 to the pilot pins 44 limits the swivel motion of the clamping lever 30 in the open position. The oblique position of the guideways 42 thereby causes the clamping lid 24 to be displaced axially in the distal direction with respect to the clamping body 10. The contact surface 26 of the clamping lid 24 thereby moves in the distal direction so far that the clamping bush 20 is axially unloaded and the clamping lid 24 does not exert any axial pressure on the clamping bush 20. If the clamping lever 30 is pivoted out of the spread open position towards the clamping body 10, the clamping lever 30 reaches the clamping position shown in FIGS. 1 and 5. In this clamping position, the clamping lever 30 bears against the clamping body 10, wherein circumferential recesses 46 and 48 of the clamping body 10 accommodate the transverse brackets 34 and 36. With this swivel motion of the clamping lever 30 into the clamping position, the guideways 42 move towards the pilot pins 44 until they strike the pilot pins 44 with their top end, as can be seen in FIG. 1. Due to the oblique position of the guideways 42, during this swivel motion the clamping lid 24 is drawn axially on the clamping body 10 in the proximal direction, as can be seen from FIGS. 1 and 5. The clamping lid 24 thereby presses with its inner contact surface 26 axially against the clamping bush 20, as is indicated by arrows in FIG. 5. Since the clamping bush 20 is supported proximally by the inner shoulder 18, the clamping bush 20 is compressed axially by the contact surface 26. Since the clamping bush 20 is supported on its outer circumference by the receptacle space 16, this axial compression causes a constriction of the inner channel 22 of the elastomeric clamping bush 20, as is indicated in FIG. 5 by the radially directed arrows.

If the clamping lever 30 is pivoted into its open position shown in FIGS. 3 and 4, the clamping bush 20 is unloaded and its inner channel 22 has a diameter corresponding to the insert opening 28 of the clamping lid 24. Now a catheter 50 can be inserted through the insert opening 28 of the clamping lid 24 into the inner channel 22 of the clamping bush 20. As soon as the catheter 50 has been inserted through the insert opening 28 and the inner channel 22 until its proximal end strikes in the clamping body 10 axially aligned with the bore 12 thereof, the clamping lever 30 is pivoted into its clamping position. The clamping bush 20 is thereby axially compressed and pressed radially over its entire axial length from the outside against the outer circumference of the catheter 50, as is shown in FIG. 5. The proximal end of the catheter 50 is thereby fixed in the clamp adapter and sealed on the outer circumference in the clamp adapter through the clamping bush 20. Now a liquid, e.g., an anesthetic, can be fed via a syringe attached to the syringe fitting 14. In order to remove the clamp adapter from the catheter 50, it is necessary only to pivot the clamping lever 30 into the open position of FIGS. 3 and 4. The clamping bush 20 is thereby axially unloaded and, due to its elasticity, again assumes its original shape, in which the inner channel 22 has the greater diameter, which renders possible a withdrawal of the catheter 50.

FIGS. 8 through 11 show a second embodiment of the clamp adapter which is suitable for a stimulation catheter. In this embodiment, the clamping mechanism corresponds fully to the clamping mechanism of the first embodiment, so that reference is made to the preceding description.

In contrast to the first embodiment, in the second embodiment a coaxial contact bush 52 also proximally adjoins the receptacle space 16 for the clamping bush 20. The contact bush 52 comprises an electrically conducting metal and has a through bore, which is axially aligned with the bore 12 of the clamping body 10 and the inner channel 22 of the clamping bush 20. The contact bush 52 is electrically connected via a conductor 54 to a connector bush 56, which is cast in a lateral fitting 58 of the clamping body 10.

In the case of a stimulation catheter, an electrically conducting wire leads in the catheter 50 to the distal tip thereof, in order to be able to locate the position of the distal catheter tip by means of electrical stimulation pulses. If the stimulation catheter is placed in the clamp adapter, the electrically conducting wire is guided out of the proximal end of the catheter 50 and bent over at the outer circumference of the catheter 50. Now the proximal end of the catheter 50 is pushed through the insert opening 28, the inner channel 22 of the clamping bush 20 up into the contact bush 52, wherein the guiding wire bent over on the outer circumference of the catheter 50 is pressed in a contacting manner against the inner circumference of the bore of the contact bush 52. In this position, the clamping lever 30 is pivoted into the clamping position, so that the catheter 50 is fixed in the clamp adapter and the guiding wire of the catheter 50 is held bearing against the contact bush 52 under pressure. A stimulation device can now be connected to the connector bush 56 in order to guide stimulation pulses via the connector bush 56, the conductor 54, the contact bush 52 and the wire of the catheter 50 to the distal catheter tip.

LIST OF REFERENCE NUMBERS

10 Clamping body
12 Bore
14 Syringe fitting
16 Receptacle space
18 Inner shoulder
20 Clamping bush
22 Inner channel
24 Clamping lid
26 Contact surface
28 Insert opening
30 Clamping lever
32 Side walls
34 Distal transverse bracket
36 Proximal transverse bracket
40 Bearing bores
42 Guideways
44 Pilot pins
46 Circumferential recess
48 Circumferential recess
50 Catheter
52 Contact bush
54 Conductor
56 Connector bush
58 Fitting

The invention claimed is:

1. A clamp adapter for a catheter, comprising:
   a clamping body, with a bore penetrating the clamping body axially, which bore continues proximally in a syringe fitting;
   a clamping bush, made of a flexibly yielding material, that can be inserted distally into the clamping body, wherein an inner channel of the clamping bush communicates with a distal end of the bore of the clamping body and a proximal end of the clamping bush is axially supported in the clamping body;
   a clamping lid, which can be placed on the clamping body distally, has an insert opening aligned with the inner channel of the clamping bush, can be moved axially with respect to the clamping body, and engages at a distal front face of the clamping bush;
   a clamping lever swivel mounted on the clamping lid about a pivot axis that runs transversely to a longitudinal axis of the clamp adapter, the clamping lever including a gripping surface at its proximal end and a transverse bracket at its distal end, the pivot axis being located between the proximal and distal ends of the clamping lever;
   a sliding block guide located proximally of the pivot axis that limits the swivel motion of the clamping lever between an open position and a closed position;
   wherein the catheter can be inserted through the insert opening of the clamping lid into the inner channel of the clamping bush and can be clamped in the inner channel by axial compression of the clamping bush by means of axial movement of the clamping lid,
   wherein the clamping lid is guided in a linearly displaceable manner with respect to the clamping body when the clamping lever is pivoted between the open position and the clamping position about the pivot axis, the clamping lever moving the clamping lid axially with respect to the clamping body by means of the distal transverse bracket bearing against an outside surface of the clamping lid such that the clamping lid axially unloads the clamping bush in the open position and axially compresses the clamping bush in the clamping position.

2. The clamp adapter according to claim 1, wherein the clamping lever is swivel mounted on the clamping lid and the sliding block guide acts between the clamping lever and the clamping body.

3. The clamp adapter according to claim 1, wherein in its open position the clamping lever is braced by the clamp adapter and in its clamping position bears against the clamp adapter.

4. The clamp adapter according to claim 1, wherein the sliding block guide has at least one guideway running obliquely to the longitudinal axis of the clamp adapter, in which guideway a pilot pin engages.

5. The clamp adapter according to claim 4, wherein at least one guideway is embodied on the clamping lever and the at least one pilot pin is embodied on the clamping body.

6. The clamp adapter according to claim 1, wherein the clamping lever has two side walls bearing against the clamping body and the clamping lid on both sides.

7. The clamp adapter according to claim 6, wherein the clamping lever can be snapped into bearing bores with journal pins formed on its sidewalls.

8. The clamp adapter according to claim 1, wherein the clamping bush is accommodated in a receptacle space of the clamping body, wherein the outer circumferential contour of the clamping bush matches the inner circumferential contour of the receptacle space.

9. The clamp adapter according to claim 8, wherein the receptacle space and the clamping bush firstly expand conically from the proximal end and then merge into a cylindrical distal section.

10. The clamp adapter according to claim 1, wherein a contact bush is placed into the clamping body proximally adjoining the clamping bush, which contact bush is connected to a plug connector for the electrical stimulation.

* * * * *